United States Patent
Delair et al.

[11] Patent Number: 6,033,853
[45] Date of Patent: Mar. 7, 2000

[54] NUCLEOTIDE SEQUENCE DETECTION WITH SIGNAL AMPLIFICATION

[75] Inventors: Thierry Delair, Echalas; Abdelhamid Elaissari, Lyons; Marie-Hélène Charles, Condrieu; Bernard Mandrand, Villeurbanne, all of France

[73] Assignee: Bio Merieux, Marcy l'Etoile, France

[21] Appl. No.: 08/952,397

[22] PCT Filed: Mar. 19, 1997

[86] PCT No.: PCT/FR97/00483

§ 371 Date: Jan. 8, 1998

§ 102(e) Date: Jan. 8, 1998

[87] PCT Pub. No.: WO97/35031

PCT Pub. Date: Sep. 25, 1997

[30] Foreign Application Priority Data

Mar. 19, 1996 [FR] France ................................. 96 03412

[51] Int. Cl.⁷ .................. C12Q 1/68; C07H 21/02; C07H 21/04; C12N 15/00
[52] U.S. Cl. .................. 435/6; 536/23.1; 536/24.3; 935/76; 935/77; 935/78
[58] Field of Search .................. 435/6, 91.2; 536/23.1, 536/24.3; 935/76, 77, 78

[56] References Cited

U.S. PATENT DOCUMENTS

| | | |
|---|---|---|
| 4,687,732 | 8/1987 | Ward et al. . |
| 4,882,269 | 11/1989 | Schneider et al. . |
| 5,512,439 | 4/1996 | Hornes et al. ................. 435/6 |
| 5,695,936 | 12/1997 | Mandrand et al. ............. 435/6 |

FOREIGN PATENT DOCUMENTS

| | | |
|---|---|---|
| 0 153 873 | 9/1985 | European Pat. Off. . |
| 0-159-719 | 10/1985 | European Pat. Off. . |
| 0 173 339 | 3/1986 | European Pat. Off. . |
| 0 204 510 | 12/1986 | European Pat. Off. . |
| 0 292 128 | 11/1988 | European Pat. Off. . |
| 0 373 956 | 6/1990 | European Pat. Off. . |
| 0-647-719 | 4/1995 | European Pat. Off. . |
| 2710075 | of 0000 | France . |
| WO 88/02784 | 4/1988 | WIPO . |
| WO 89/03849 | 5/1989 | WIPO . |
| WO 90/00622 | 1/1990 | WIPO . |
| WO91/08307 | 6/1991 | WIPO . |
| WO 94/00600 | 1/1994 | WIPO . |
| WO 95/08000 | 3/1995 | WIPO . |

OTHER PUBLICATIONS

Pieles, U., et al., "A protected biotin containing deoxycytidine building block for solid phase synthesis of biotinylated oligonucleotides", *Nucleic Acids Research*, vol. 18, No. 15, 1990, pp. 4355–4360.

Misiura K., et al., "Biotinyl and phosphotyrosinyl phosphoramidite derivatives useful in the incorporation of multiple reporter groups on synthetic oligonucleotides", *Nucleic Acids Research*, vol. 18, No. 15, 1990, pp. 4345–4354.

The Stratagene Catalog p. 39 (1988).

*Primary Examiner*—W. Gary Jones
*Assistant Examiner*—Ethan Whisenant
*Attorney, Agent, or Firm*—Oliff & Berridge, PLC

[57] ABSTRACT

Kit for detecting a specific target nucleic acid sequence using a labeled probe with signal amplification, which comprises in containers (i) a probe labeled with a tracer (ii) a suspension of insoluble particles on which are immobilized at least one series of oligonucleotide units all of which are identical and contain at least one sequence that specifically hybridize with the target nucleic acid sequence and at one sequence that specifically hybridize with tracer labeled probe. A method using the kit is also described.

12 Claims, 1 Drawing Sheet

NUCLEOTIDE SEQUENCE DETECTION WITH SIGNAL AMPLIFICATION

This application is a 371 of PCT/FR97/00483 filed Mar. 19, 1997.

The subject of the present invention is a reagent and a process for the detection of a nucleotide sequence in a sample.

It is often necessary to determine if a gene, a gene portion or a specific nucleotide sequence is present in a living organism, in a cellular extract or in biological samples.

The search for specific nucleotide sequences is used in particular for the detection of pathogenic organisms, the determination of the presence of alleles or the detection of the presence of lesions in a genome. Genetic diseases such as Huntington's disease, Duchenne's myopathy, phenylketonuria and β-thalassaemia can be diagnosed through the analysis of DNA from individuals. Furthermore, the diagnosis or the identification of viruses, of viroids, of bacteria, of fungi or of parasites can be carried out by hybridization experiments with nucleic probes.

Various types of methods of detection of nucleic acids are described in the literature. These methods are based on the purine-pyrimidine pairing properties of the complementary strands of nucleic acids in DNA—DNA, DNA-RNA and RNA—RNA duplexes. This pairing process occurs through the establishment of hydrogen bonds between the adenosine-thymine (A-T) and quanosine-cytosine (G-C) bases of the double-stranded DNA. Adenosine-uracil (A-U) base pairs can also be formed through hydrogen bonds in DNA-RNA or RNA—RNA duplexes. The pairing of nucleic acid strands for the determination of the presence or of the absence of a given nucleic acid molecule is commonly called "hybridization of nucleic acids" or simply "hybridization".

On the basis of the properties of nucleic acids, techniques have been developed which make it possible to detect and quantify, in a sample to be analysed, a nucleic acid called target. These techniques, which are well known, can be divided into two main groups: the so-called direct detection techniques such as that of the so-called SOUTHERN technique and the so-called "Dot-blot" technique for the detection of DNA or the NORTHERN technique for the detection of RNA, and the so-called indirect techniques such as the sandwich or "Reverse-Dot" technique.

One of the principal difficulties encountered during the development of a test for detecting a target nucleotide sequence of interest is the sensitivity threshold of the hybridization methods, and various methods have been described in order to increase the power of detection of these hybridization techniques. These so-called "amplification" methods can be used at various stages of a detection process using nucleic probes. Two categories can be distinguished: amplification of a target or of a signal.

The techniques for amplification of a target are known. One disadvantage of these techniques lies in the difficulty of quantifying the nucleic target of interest after the amplification step.

Other approaches, relating to the amplification of a signal, have been described. Thus, U.S. Pat. No. 4,731,325 and EP-0,225,807 describe techniques using a plurality of detection probes which can hybridize to the target. In many cases (necessity to differentiate between related species in bacteriology or detection of genetic diseases), it is not possible to use this technique because only one specific sequence on the target is capable of being used to hybridize a detection probe.

Some techniques described consist in increasing the number of markers, that is to say of molecules capable of generating a signal, directly or indirectly, on the detection probe. The marker may be in particular a biotin, a fluorophore, an enzyme or a radioactive group. The detection probe is grafted onto a polymer, which may be of a nucleotide nature, onto which are attached, most often through covalent bonding, a number of markers greater than two (see for example U.S. Pat. No. 4,687,732, EP-0,373,956, WO-88/02784, WO-90/00622, EP-0,292,128, WO-89/03849 and EP-0,173,339).

One of the disadvantages of these techniques lies in the need to carry out controlled coupling between the probe and the number of markers. This double coupling is not easy to control in order to have a maximum of markers for a detection probe. Systems where the marker is incorporated in a controlled manner, for example during the automatic synthesis of oligodeoxyribonucleotides, have been described (Pieles U. et al., Nucleic Acids Research, 18, 4355–4360 (1990) or Misiura K. et al., Nucleic Acids Research, 18, 4345–4354 (1990)). However, in this case, the number of markers incorporated is low because of limitations inherent in synthesis on a solid support. Furthermore, when the number of markers increases, the detection probe is easily masked by the markers and the hybridization yield decreases.

These same disadvantages are found in the system described in U.S. Pat. No. 4,882,269. A so-called primary probe of a nucleotide nature comprising a polymer-type tail of any type hybridizes with the target. This tail may carry a marker which can be revealed by a suitable secondary probe. In the case where the tail is of a nucleotide nature, the secondary probe is of a nucleotide nature and can hybridize with the tail. For the system to function, a large-sized nucleotide tail, having a sequence different from the primary probe, is required and the labelled secondary probes should be multiplied.

This is achieved in practice by molecular biology techniques where the primary probe is cloned into a phage and the secondary probes are complementary to various sequences of the phage.

Another system is described in patent EP-0,153,873, in which a portion of a so-called primary nucleic probe hybridizes with the target. This primary probe comprises a second portion with which a so-called secondary multilabelled second probe can become hybridized. In the practical application, these primary probes are manufactured by molecular biology techniques such as cloning (for example cloning of a sequence specific for the target into a fragment of phage M13) which are not very suitable for large-scale manufacturing processes.

The document EP-0,204,510 describes a process in which the nucleic target is brought into contact with a first probe called receptor probe, a second probe called amplification probe and a third probe, called labelled probe, capable of hybridizing with the second amplification probe. The receptor probe which hybridizes with the target possesses a homopolymeric nucleotide tail (for example polyA). The amplification probe contains a sequence complementary to the tail (for example polyT). The labelling probe contains a nucleotide sequence capable of hybridizing with the amplification probe (for example labelled polyA). This combination of probes constitutes a cluster leading to signal amplification. Another type of cluster is described in patent EP-0,450,594. In these two cases, the clusters which are produced in the hybridization medium are not controlled and lead to a poor reproducibility and therefore to quantification problems. Furthermore, the multiplication of successive hybridization steps leads to losses which lead to a poor gain in signal amplification.

In patent FR-2,710,075, there is described the use of a copolymer onto which are grafted several oligonucleotide units which are complementary to a labelled detection probe and which are also complementary to the target. However, the polymers tend to form aggregates which interfere with the homogeneity of the results.

A detection system has now been found which does not exhibit the abovementioned disadvantages.

The subject of the invention is a kit for the detection of a nucleotide sequence of interest with the aid of a labelled nucleotide probe, with signal amplification, characterized in that it contains, in appropriate containers, the said nucleotide probe, labelled with a marker, and a reagent essentially comprising a suspension of particles on which is immobilized at least one series of oligonucleotide units, each of the said oligonucleotide units of the said series, all identical, comprising, at least, a nucleotide sequence capable of hybridizing with the said sequence of interest and a nucleotide sequence capable of hybridizing with the said probe, the said reagent containing more than 10, and in particular more than 50, of the said oligonucleotide units of the said series per particle.

Of course, the number of nucleotide units given here is an average number of nucleotide units per particle.

For example, the reagent used in the kit of the invention may comprise, on average, from 100 to 1000 of the said oligonucleotide units of the same series per particle.

The suspension of particles is also called "latex". Latex here denotes a suspension of particles of polymer, natural or synthetic, in a liquid medium, particularly an aqueous medium, the particles being insoluble in the said medium and having sizes of less than 10 μm.

The latex particles which can be used in the preparation of the reagent may be commercial products or may be prepared in a known manner, particularly by polymerization in emulsion, suspension, dispersion, or by precipitation; see for example R. Arshady, Colloid Polym. Sci. 270:717–732 (1992) and patent FR-2,676,451. These particles may carry reactive functions such as for example thiol, amine or carbonyl (particularly aldehyde) groups; carboxylic acid groups, activated carboxylic acid groups, particularly in acid chloride, anhydride, mixed anhydride, or ester (N-hydroxysuccinimide ester, p-nitrophenyl ester and the like) form; hydroxyl groups and derivatives thereof (tosylates, mesylates and the like); halogenated groups; activated double bonds (for example divinylsulphone; α,β-unsaturated carbonyl groups and the like). The polymeric material constituting the particles may be derived in particular from monomers chosen from vinyl-type derivatives such as styrene, acrylic derivatives (acrylic and methacrylic acids, acrylamides and methacrylamides, acrylic and methacrylic esters), alcohols, vinyl esters and ethers, and the like).

The particles, which are preferably homogeneous in size, have for example sizes which may range from 50 nm to 5 μm, and in particular from 100 to 1000 nm.

The term "oligonucleotide unit" as used in the present application designates an oligonucleotide consisting of a chain of at least 5 deoxyribonucleotides or ribonucleotides optionally comprising at least one modified nucleotide, for example at least one nucleotide comprising a modified base such as inosine, 5-methyldeoxycytidine, 5-dimethylaminodeoxyuridine, deoxyuridine, 2,6-diaminopurine, 5-bromodeoxyuridine or any other modified base allowing hybridization. This oligonucleotide may also be modified at the level of the internucleotide bond such as for example the phosphorothioates, the H-phosphonates, the alkyl phosphonates, at the level of the backbone such as for example the α-oligonucleotides (FR-2,607,507) or the PNAs (M. Egholm et al., J. Am. Chem. Soc., (1992), 114, 1895–1897). These various modifications can optionally be taken in combination.

The sequence of interest is particularly a single-stranded nucleotide sequence, optionally obtained by prior denaturation of a hybrid (DNA—DNA, DNA-RNA or RNA—RNA) according to conventional (physical, chemical or enzymatic) techniques. The signal amplification system of the invention can also serve for the detection of a double-stranded sequence, the procedure being carried out according to the triple helix technique to which it can be applied.

The markers used to label the detection probe are chosen from the customary markers. They are, for example:

enzymes which are capable of producing a signal detectable for example by colorimetry, fluorescence or luminescence, such as horseradish peroxidase, alkaline phosphatase, β-galactosidase, glucose-6-phosphate dehydrogenase and the like;

chromophores such as fluorescent, luminescent or colouring compounds;

groups with an electron density detectable by electron microscopy or by their electrical properties such as conductivity, amperometry, voltametry or impedance measurements;

groups detectable by optical methods (such as diffraction, surface plasmon resonance, contact angle variation) or by physical methods such as atomic force spectroscopy, tunnel effect;

radioactive molecules such as $^{32}P$, $^{35}S$ or $^{125}I$.

Covalent or noncovalent methods for attaching these markers depend on the type of marker and are well known.

Indirect systems can also be used, for example those comprising haptens, detectable by a specific antibody, or a protein such as the biotin-avidin or biotin-streptavidin pair, or alternatively a sugar/lectin pair. In this case, it is the antibody or the protein which carries a marker.

The DNA/DNA, RNA/RNA, DNA/RNA type hybrid nucleic acids can be detected by antihybrid antibodies, or by specific proteins such as phage polymerases.

If the detection probe consists of modified nucleotides such as the alpha anomeric nucleotides or the PNAs (P. E. NIELSEN et al., Science, 254,1497–1500 (1991)), anti-alpha-nucleotide or anti-PNA antibodies can be used.

According to a first embodiment, the reagent used according to the invention is characterized in that, in the same oligonucleotide unit, the said sequences capable of hybridization are distinct and nonoverlapping. In such a case, the sequence of the labelled probe may be chosen arbitrarily, and the said oligonucleotide sequence capable of hybridizing with the probe is then a sequence complementary to that of the probe.

In a system using such a reagent, the labelled probe can therefore be used as universal detection probe. In addition, such a system is more particularly suitable for carrying out the detection in a single step, particularly with no intermediate wash(es).

In another embodiment, the reagent used according to the invention is characterized in that, in the same oligonucleotide unit, one of the said sequences capable of hybridization is nested in the other. In other words, one of the said sequences consists of a portion of the other sequence, or alternatively, in the extreme case, both sequences are indistinguishable (they are identical) and, in fact, are one and the same, in the oligonucleotide unit. In this embodiment, the labelled probe should obviously be adapted to the target (sequence of interest): either the probe is identical to the sequence of interest, or the probe should at least be homologous to the sequence of interest, that is to say be capable of hybridizing with the sequence complementary to the sequence of interest.

Generally, the reagent used according to the invention contains a few hundreds of oligonucleotide units of the same series (all identical), particularly 100 to 1000 oligonucleotide units, as defined above, per particle. This reagent is also called here "detection conjugate".

The oligonucleotide units present in the amplification reagent of the invention are generally oligonucleotides which are from 5 to 100 nucleotides long and in particular from 10 to 40 nucleotides long.

The oligonucleotide units are immobilized on the latex particles according to known methods, for example by adsorption, by hydrophobic interaction, by ionic interaction, or by the establishment of hydrogen bonds, or alternatively by coupling so as to establish a covalent bond with the particles, optionally through a spacer arm.

The coupling of oligonucleotide units with the latex particles may be performed according to one of the following methods. For example, in the case of a direct method, an oligonucleotide is synthesized which has a reactive functional group at any site of the nucleotide chain, such as for example at the 5' end or at the 3' end, or on a nucleotide base or on an internucleotide phosphate, or alternatively in the 2'-position of the nucleotide sugar. The oligonucleotide is then coupled to the latex particles prepared beforehand and comprising a reactive functional group complementary to that of the oligonucleotide, that is to say such that the reaction of the two reactive functional groups with each other allows the establishment of a covalent bond between the oligonucleotide and a particle. By way of examples of pairs of reactive functional groups, there may be coupled primary amines with an activated carboxylic acid, an aldehyde, an isocyanate, an isothiocyanate or a double bond activated by at least one carbonyl, by a sulphone, by a sulphoxide group or by a nitrile; or alternatively a thiol functional group with a haloalkyl or with a derivative having an activated carbon—carbon double bond.

In an indirect coupling method, the oligonucleotide and the particles are each carriers of a reactive functional group, it being possible for these reactive functional groups to be identical or different from each other, these two functional groups not being complementary, but being capable of reacting with an intermediate coupling agent which is a bifunctional reagent which may optionally play the role of spacer arm. This agent is said to be homobifunctional if the two functional groups are identical and heterobifunctional if the two functional groups are different. Among the homobifunctional coupling agents, there may be mentioned DITC (1,4-phenylene diisothiocyanate), DSS (disuccinimidyl suberate) and the like when the two reactive functional groups are primary amine functional groups. Among the heterobifunctional coupling agents, there may be mentioned SMCC (succinimidyl 4-(N-maleimidomethyl)cyclohexane-1-carboxylate) when the two reactive functional groups each have, independently of the other, a primary amine functional group and a thiol functional group, SMPB (succinimidyl 4-(p-maleimidophenyl)butyrate) and the like.

After the coupling of the oligonucleotide with the particles, any excess reactive functional group on the particles can be neutralized, where appropriate, in a manner known per se. For example, the excess aldehyde groups can be neutralized with a primary amine such as ethanolamine (and conversely), the maleimide groups may be neutralized with a thiol (such as thioethanolamine or dithiothreitol), and the like.

It is possible to immobilize in the same manner, on particles coupled to a first series of oligonucleotide units which are all identical, at least one second series of oligonucleotide units which are all identical but different from those of the first series. For example, the oligonucleotide units of the second series comprise a nucleotide sequence capable of hybridizing with a second sequence of interest which is different from the sequence of interest recognized by the oligonucleotide units of the first series.

The invention also relates to the use of a reagent, consisting of the detection conjugate as defined above, as signal amplification reagent in a process for the detection of a nucleotide sequence of interest.

The sequence of interest is either a sequence of the target substance (that which it is effectively desired to detect), or a sequence bound to the target substance, or else (in competition methods) a sequence bound to an analogue of the target substance, which is a competitor for the latter.

The invention relates in particular to a process for the detection, with signal amplification, of a nucleotide sequence of interest capable of being immobilized on a solid support, in which a detection nucleotide probe labelled with a marker is used, characterized in that there are added to a liquid medium in contact with the said solid support, under conditions allowing the hybridization:

a reagent as defined above, and the labelled detection probe, and the possible presence of the marker immobilized on the solid support is then revealed according to the customary methods.

The term "solid support" as used here includes all materials on which an oligonucleotide may be immobilized for use in diagnostic tests, in affinite chromatography and in separation processes. Natural or synthetic materials, chemically modified or otherwise, can be used as solid support, particularly polysaccharides such as cellulose-based materials, for example paper, cellulose derivatives such as cellulose acetate or nitrocellulose, dextran; polymers such as polyvinyl chlorides, polyethylenes, polystyrenes, polyacrylates, polyamides, or copolymers based on aromatic vinyl monomers, alkyl esters of α-β-unsaturated acids, esters of unsaturated carboxylic acids, vinylidene chloride, dienes or compounds having nitrile functional groups (such as acrylonitrile); polymers of vinyl chloride and of propylene; polymers of vinyl chloride and of vinyl acetate; copolymers based on styrenes or substituted derivatives of styrene; natural fibres such as cotton and synthetic fibres such as nylon; inorganic materials such as silica, glass, ceramic, quartz. The choice of a support material, in each specific case, may be made using simple routine experiments.

The solid support used in the present invention is in particular a polystyrene polymer, a butadiene-styrene copolymer or a butadiene-styrene copolymer mixed with one or more polymers or copolymers chosen from polystyrene, styrene-acrylonitrile or styrene-methyl methacrylate copolymers, polypropylenes, polycarbonates and the like. The solid support used is in particular a polystyrene or a styrene-based copolymer comprising between about 10 and 90% by weight of styrene units.

The solid support used may be, in the appropriate customary forms, for example, in the form of a microtitre plate, a sheet, a cone, a tube, a well, beads and the like.

The process of the invention can serve for the detection and/or assay of a target nucleic acid fragment which may be present in a sample, particularly in the cases already mentioned in the introduction of the present application: diagnosis of genetic diseases, identifications of pathogenic agents such as bacteria, viruses, fungi or parasites and the like. The nucleotide sequence of interest is a determined portion of the nucleotide sequence of the target, which may be chosen, in particular, as means for characterizing a species, a genus, an allele and the like. The nucleotide sequence of interest is attached to the solid support directly or indirectly by means of a ligand. The ligand may be in particular a capture probe chosen to be complementary to another region of the target, according to the sandwich technique, which is well known. In another embodiment of the sandwich technique, the capture probe is itself grafted onto a copolymer immobilized or capable of being immobilized on the solid support, for example by passive adsorption, that is to say without the formation of a covalent bond between the support and the copolymer carrying the capture probe. This method can contribute towards reducing the background noise. The sequence of interest can also be attached directly to the solid support by means of the target according to the "Reverse-Dot" technique.

The process of the invention is also applicable to immunoassays and in particular to the detection of haptens, of antigens, of polypeptides or of antibodies, in processes with or without competition. For example, an oligonucleotide may be grafted, preferably by a covalent bond, onto a ligand capable of reacting specifically with a target molecule. This oligonucleotide then plays the role of "sequence of interest". In the competition techniques, the oligonucleotide may be grafted, preferably through covalent bonding, onto a ligand, the said ligand being capable of entering into competition with the target for its attachment to a specific anti-ligand. The techniques for coupling between a ligand and the oligonucleotide depend on the nature of the ligand and are well known. It is obviously necessary to choose a coupling method which does not alter the capacity of the ligand to recognize the anti-ligand, which can be easily checked by simple routine experiments.

The term "antibody" designates in particular monoclonal or polyclonal antibodies, antibody fragments and antibodies obtained by genetic recombination.

The term "hapten" designates a molecule whose size is insufficient to be an immunogen, but which, through coupling with a protein, for example, allows, by immunization of animals, the production of antibodies recognizing the said molecule.

By way of illustration, if the target to be assayed is an antigen, the sequence of interest (that is to say the oligonucleotide) is grafted onto an antibody specific for the antigen. This antibody, after reacting with the antigen, can react via the sequence of interest to form a complex with the reagent oligonucleotides-latex. The oligonucleotide unit grafted onto the latex particles comprises a sequence complementary to at least a portion of the sequence of interest. With a labelled detection probe, it is thus possible to reveal the antigen with good sensitivity, by virtue of the amplification of the signal.

If the oligonucleotide unit of the reagent comprises a sequence specific for the sequence of interest and another sequence, this other sequence will be complementary to the sequence, which is arbitrary, of the probe. A reduction in the number of steps is possible by using an appropriate buffer allowing both the reaction of the ligand with the anti-ligand and the hybridization of the nucleotide sequences with each other. An assay in a single step can be carried out, the antibody being grafted onto the sequence of interest, the detection reagent latex-oligonucleotides and the detection probe reacting during the same incubation.

BRIEF DESCRIPTION OF THE DRAWING

In the accompanying drawing, the single figure (FIG. 1) is a graph representing the variation in signal with amplification (-♦-) and without amplification (-□-) in the assay described in Example 2 below. The quantity of target DNA copies, expressed as powers of 10, is plotted on the x-axis, and the signal expressed as relative fluorescence units (RFU) on the y-axis.

The following examples illustrate the invention. In these examples, the nucleotide sequences used are the following:

Figure 1:
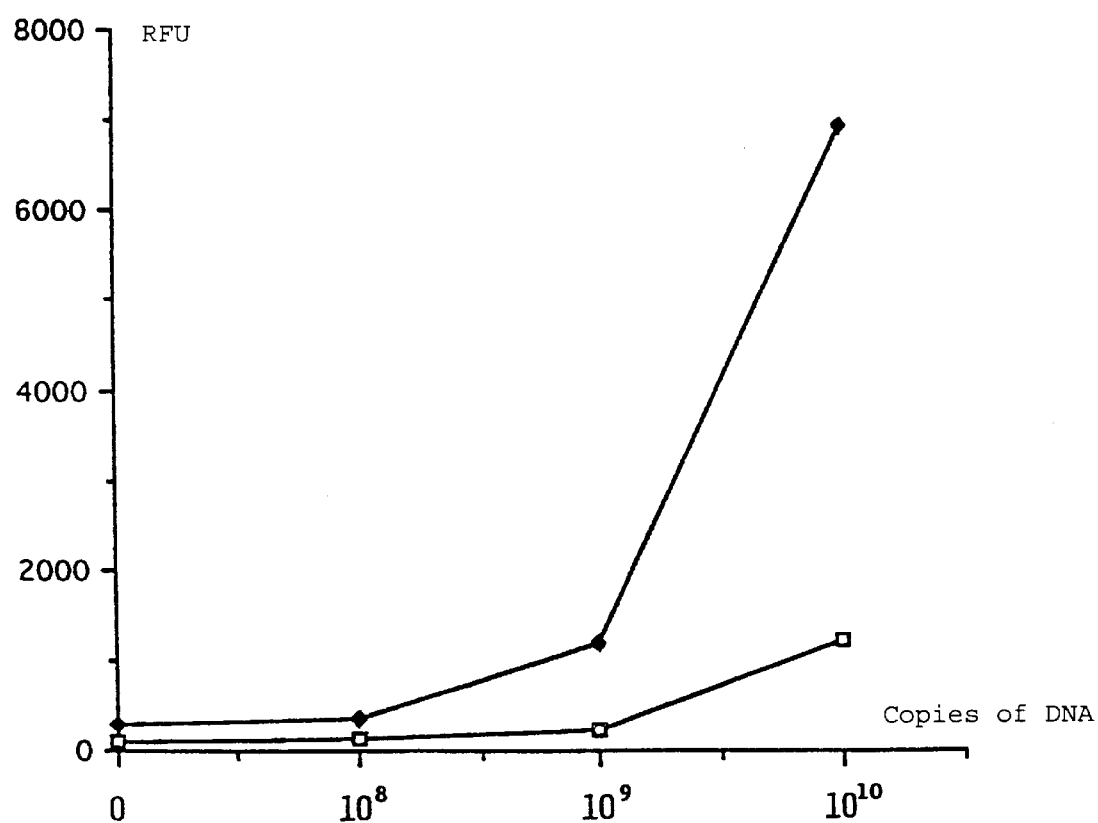

```
sequence 3059:
TCAATCTCGGGAATCTCAATGTTAG        SEQ ID NO. 1 sequence 2908:
AACGCTACTACTATTAG                SEQ ID NO. 2 sequence 3057:
CTACTAATAGTAGTAGCGTT             SEQ ID NO. 3
```

EXAMPLES

Example 1

Coupling of an oligonucleotide with latex particles

The oligonucleotide 2908 is activated beforehand with phenylenediisothiocyanate under the following conditions: 30 nanomoles of oligonucleotide are dissolved in 25 µl of 0.1 M sodium borate buffer pH 9.3 to which there are added 60 µl of a solution of phenylenediisothiocyanate (DITC) in dimethylformamide at 30 g/l. After incubating for 2 hours at 37° C., the unreacted DITC is extracted with butanol and then the aqueous phase is recovered and it is evaporated to dryness under reduced pressure. The activated oligonucleotide 2908 is thus obtained.

A latex is added to a 0.1 M sodium carbonate buffer, pH 9.3, containing the activated oligonucleotide 2908 so as to obtain a suspension containing 1% by weight of particles and 100 µg of oligonucleotide 2908 per ml.

The latex was obtained in a manner similar to that described in Example 1 of patent FR-2,676,451, starting with a mixture of styrene and aminomethylstyrene hydrochloride, containing 1% by weight of the latter (which is itself a 60:40 mixture, in moles, of the para and meta isomers). The particles have mean sizes of the order of 430 nm.

After stirring for 15 hours, the mixture is centrifuged and the centrifugation pellet is taken up in a 0.1 M glycine buffer, pH 8.2, containing 0.15 M NaCl.

The coupling yield is determined by assaying (by UV at 280 nm) the quantity of residual oligonucleotides in the supernatant after centrifugation of the latex. This yield is of the order of 70%.

Example 2

Detection of a nucleic acid fragment of the hepatitis B virus by the sandwich protocol on an automatic VIDAS machine using for the detection oligonucleotides coupled to latex particles obtained in Example 1 above.

The following protocol is carried out automatically on the automatic VIDAS® machine marketed by the company bioMérieux-Vitek.

The reaction is carried out in a conical support called SPR ("Solid Phase Receptacle"), made from a material sold under the name "K résine" (butadiene-styrene copolymer) and marketed by the company bioMérieux-Vitek (USA). The various reagents are placed in different wells of a strip and the successive steps are carried out in the SPR which serves as pipette. The sandwich-hybridization reaction described in the protocol below takes place on the inner wall of the cone.

Oligonucleotide 3059 (specific for the DNA of the hepatitis B virus) coupled to a copolymer (described in Example 1 of FR-2,710,075) is passively attached to the inner surface of the SPR. The concentration used is 0.15 nmol/ml of oligonucleotides in a volume of 300 µl of a 4× PBS solution (200 mM sodium phosphate, pH 7.0, 600 mM NaCl). After 18 hours at room temperature, or two hours at 37° C., the cones are washed twice with a PBS-Tween solution, and then dried under vacuum.

The strip contains all the reagents necessary for the detection, in independent wells, that is to say:

well 2: 100 µl of a solution containing 0.015 nmol/ml of oligonucleotide 2908 bound to the latex particles, in a PEG buffer (150 mM sodium phosphate, 450 mM NaCl, pH 7+0.14 mg/ml of salmon sperm DNA (Sigma D 9156)+20 g/l of PEG 4000 (Merck 807490)+6.5 g/l of Tween 20 (Biorad 1706531)), well 3: 200 µl of a solution containing 0.045 nmol/ml, in the PEG buffer, of the detection probe. The detection probe is the oligonucleotide 3057, coupled to alkaline phosphatase as described in WO-91/19812, wells 4 and 5: twice 600 µl of PBS-Tween washing solution, well 6: 300 µl of MUP (4-methylumbelliferyl phosphate) substrate in solution in a diethanolamine buffer.

200 µl of the solution of target in a PEG buffer are deposited in the first well (well 1) of the strip. After mixing, reconstituted in well 2, target (110 µl from well 1), detection probe and oligonucleotide-latex conjugate for the amplification (110 µl from well 3), and incubation for 45 minutes of the cone containing the said mixture, the cone is washed twice with a solution of PBS-Tween. 250 µl of substrate are aspirated into the cone for 15 minutes and then released into a reading cuvette. The apparatus measures the fluorescent signal expressed in RFU (relative fluorescence units).

By way of comparison, a similar assay was carried out, but omitting the addition of the 2908-latex conjugate to well No. 2.

The results are presented in FIG. 1.

We claim:

1. A kit for the detection of a target nucleotide sequence with signal amplification, wherein, in appropriate containers, said kit comprises:
 a) a nucleotide probe that is labeled with a marker, and
 b) a reagent comprising a suspension of insoluble particles wherein at least one series of oligonucleotide units is immobilized on said particles; wherein within each said series said oligonucleotide units are identical and comprise:
 a first nucleotide sequence that specifically hybridizes with said target nucleotide sequence, and
 a second nucleotide sequence that specifically hybridizes with said nucleotide probe; and
 wherein said reagent has more than 10 of said oligonucleotide units per particle.

2. A kit according to claim 1, wherein said first nucleotide sequence is distinct and nonoverlapping with said second nucleotide sequence in a single oligonucleotide unit.

3. A kit according to claim 1, wherein one of said first and said second nucleotide sequences comprises the other of said first and said second nucleotide sequences.

4. A kit according to claim 1, wherein said first nucleotide sequence and said second nucleotide sequence are identical.

5. A kit according to claim 1, wherein said reagent has on average from about 100 to 1000 of said oligonucleotide units per particle.

6. A kit according to claim 1, wherein the size of said particles is less than 10 µm.

7. A kit according to claim 6, wherein the size of said particles ranges from 50 nm to 5 µm.

8. A kit according to claim 6, wherein the size of said particles ranges from 100 nm to 1000 nm.

9. A method for detecting with signal amplification a target nucleotide sequence comprising adding to a liquid medium under conditions allowing hybridization, a nucleotide probe that is labeled with a marker, and a reagent comprising a suspension of insoluble particles wherein at least one series of oligonucleotide units is immobilized on said particles; wherein within each said series said oligonucleotide units are identical and comprise:
 a first nucleotide sequence that specifically hybridizes with said target nucleotide sequence, and
 a second nucleotide sequence that specifically hybridizes with said nucleotide probe;
 wherein said reagent has more than 10 of said oligonucleotide units per particle; and
 wherein the presence of target nucleotide sequence is detected.

10. A method according to claim 9, wherein said reagent and said probe are added to said liquid medium without an intermediate washing step.

11. A method according to claim 10, wherein said reagent and said probe are added to said liquid medium at the same time.

12. A method according to claim 9 wherein said target nucleotide sequence is immobilized on a solid support, and said liquid medium is in contact with said solid support.

* * * * *

SEQUENCE LISTING

```
(1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

TCAATCTCGG GAATCTCAAT GTTAG                                              25

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AACGCTACTA CTATTAG                                                       17

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

-continued

```
    (ii) MOLECULE TYPE: DNA (genomic)

(xi) SEQUENCE DESCRIPTION: SEQ ID NO:3:

CTACTAATAG TAGTAGCGTT                                              20
```